United States Patent
Burch

(10) Patent No.: US 6,726,908 B2
(45) Date of Patent: *Apr. 27, 2004

(54) PHARMACEUTICAL FORMULATION

(75) Inventor: Daniel Joseph Burch, Collegeville, PA (US)

(73) Assignee: SmithKline Beecham p.l.c. (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 96 days.

(21) Appl. No.: 08/722,259

(22) PCT Filed: Oct. 27, 1997

(86) PCT No.: PCT/US96/14554

§ 371 (c)(1),
(2), (4) Date: Oct. 27, 1997

(87) PCT Pub. No.: WO97/09042

PCT Pub. Date: Mar. 13, 1997

(65) Prior Publication Data

US 2001/0043926 A1 Nov. 22, 2001

Related U.S. Application Data

(60) Provisional application No. 60/003,353, filed on Sep. 7, 1995.

(51) Int. Cl.$^7$ .............................................. A61K 35/00
(52) U.S. Cl. ...................................................... 424/114
(58) Field of Search ......................................... 424/114

(56) References Cited

U.S. PATENT DOCUMENTS

| | | | |
|---|---|---|---|
| 4,282,202 A | 8/1981 | Dowrick | |
| 4,301,149 A | * 11/1981 | Crowley | 424/114 |
| 4,441,609 A | 4/1984 | Crowley | |
| 4,525,352 A | 6/1985 | Cole et al. | 424/114 |
| 4,537,887 A | 8/1985 | Rooke et al. | |
| 4,673,637 A | 6/1987 | Hyman | |
| 5,733,577 A | 3/1998 | Myers et al. | |
| 5,962,022 A | 10/1999 | Bolt et al. | |
| 6,051,255 A | 4/2000 | Conley et al. | |
| 6,077,536 A | 6/2000 | Merrifield et al. | |

FOREIGN PATENT DOCUMENTS

| | | |
|---|---|---|
| EP | 0 080 862 | 11/1982 |
| EP | 0080862 | 11/1982 |
| EP | 0281200 A | 2/1988 |
| EP | 0389177 A | 3/1990 |
| EP | 1 044 680 A1 | 10/2000 |
| GB | 2 005 538 | 4/1979 |
| HU | 205611 B | 4/1991 |
| WO | WO 91/15197 | 10/1991 |
| WO | WO 92/19227 | 11/1992 |
| WO | WO 93/00898 | 1/1993 |
| WO | WO 94/16696 | 8/1994 |
| WO | WO 9416696 * | 8/1994 ................. 424/114 |
| WO | WO 94/27557 | 12/1994 |
| WO | WO 94/27600 | 12/1994 |
| WO | WO 98/20946 | 8/1995 |
| WO | WO 95/25516 | 9/1995 |
| WO | WO 95/28148 | 10/1995 |
| WO | WO 95/28927 | 11/1995 |
| WO | WO 95/33487 | 12/1995 |
| WO | WO 96/04907 | 2/1996 |
| WO | WO 96/04908 | 2/1996 |
| WO | WO 96/07408 | 3/1996 |
| WO | WO 96/34605 | 11/1996 |
| WO | WO 97/09042 | 3/1997 |
| WO | WO 98/35672 | 8/1998 |
| WO | WO 98/40054 | 9/1998 |
| WO | WO 98/42311 | 10/1998 |
| WO | WO 00/03695 | 1/2000 |
| WO | WO 00/12088 | 3/2000 |

OTHER PUBLICATIONS

Arguedas et al., J. Antimicrob. Chemother., 27(3), 311–18, Abstract Only, 1991.*

Legent et al., Chemotherapy(Basel), 40(Suppl. 1), 8–15 Abstract Only, 1994.*

Dagan et al., Bacteriological and Clinical Efficacy of a New Amoxicillin/Clavulanate formulation (A/C–ES) in the Treatment of Acute Otitis Media (AOM) Abstract (2000).

Robison, "Amoxicillin trihydrate/Clavulanic acid potassium salt", Med. Actual., 1982, 18(5) pp. 213–219.

Chan et al., "A comparative study of amoxicillin–clavulanate and amoxicillin. Treatment of otitis media with effusion." Archives of Otolaryngology—Head and Neck Surgery, Feb. 1988, 114(2), pp. 142–146.

Pichichero, "Resistant respiratory pathogens and extended–spectrum antibiotics", American Family Physician, 1995, 52(6), pp. 1739–1746.

Hol et al., "Experimental evidence for Moraxella–induced penicillin neutralization in pneumococcal pneumonia", Journal of Infectious Diseases, 1994, 170(6), pp. 1613–1614.

Baron et al., "Antimicrobial therapy in acute otitis media", Traitement Antibiotique de L'Otite Moyenne Aigue, Annales de Pediatrie, 1991, 38(8), pp. 549–555.

Neville, "Augmentin: An in vitro study of bacterial sensitivities to a synergistic combination", New Zealand Medical Journal, 1982, 95(714), pp. 579–581.

Pegler et al., "Augmentin treatment of bacterial infections in hospitalized patients", New Zealand Medical Journal, 1982, 95(713), pp. 542–545.

Woodnutt et al, Antimicrobial Agents and Chemotherapy, "Efficacy of High–Dose Amoxicillin–Clavulanate against Experimental Respiratory Tract Infections Caused by Strains of *Streptococcus pneumonia*" 43(1), 35–40, (1999).

(List continued on next page.)

Primary Examiner—Jerome D. Goldberg
(74) Attorney, Agent, or Firm—Dara L. Dinner; Stephen Venetianer; Charles M. Kinzig

(57) ABSTRACT

This invention relates to pharmaceutical formulations comprising amoxycillin and a salt clavulanic acid in a ratio of 14:1.

56 Claims, 3 Drawing Sheets

OTHER PUBLICATIONS

Bottenfield et al., "Safety and Tolerability of a New Formulation . . . in the Empiric Treatment of Pediatric . . . *Streptococcus pneumoniae,"Pediatr. Infect. Dis. J.*, vol. 17, pp. 963–968 (1998).

Amendola et al., "Pediatric suspension of amoxycillin and clavulanic acid in the treatment of bacterial infections of the upper respiratory tract and ear", Minerva Pediatrics, 1989, vol. 41, No. 2, pp. 97–103.

Astruc et al., "Efficacy and tolerance of a new formulation amoxicillin 100 mg—clavulanic acid 12.5 mg in acute otitis media in infants", Annales De Pediatrie, 1992, vol. 39, No. 2, 142–148.

Aulton et al., "The Mechanical Properties of Hydroxypropyimethylcellulose Films Derived from Aqueous Systems", Drug Development and Industrial Pharmacy, 1981, 7(6), 649–668.

Beghi et al., "Efficacy and Tolerability of Azithromycin versus Amoxicillin/Clavulanic Acid in Acute Purulent Exacerbation of Chronic Bronchitis", Journal of Chemotherapy, 1995, 7(2), pp. 146–152.

Behre et al., "Efficacy of Twice–Daily Dosing of Amoxycillin/Clavulanate etc.", Infection, 3, pp. 163–168 (1995).

Cook et al., "Efficacy of Twice–Daily Amoxycillin/Clavulanate etc.", BJC, 50(3), 1996, pp. 125–128.

Cooper et., "Effect of low concentrations of clavulanic acid on the in–vitro activity of amoxycillin against B–lactamase–producing Branhamelia catarrhalis and Haemophilus influenzae", Journal of Antimicrobial Chemotherapy, 1990, vol. 26, pp. 371–380.

Ellis–Pegler et al., "Augmentin treatment of bacterial infections in hospitalized patients", New Zealand Medical Journal, 1982, 95(713), pp. 542–545.

Feldman et al., "Twice–daily antibiotics in the treatment of acute otitis trimethoprim–sulfamethoxazole versus amoxicillin–clavulanate", Can Med. Assoc. J., 1990, 142(2), pp. 115–118.

Fink et al., "A trial of orally administered Augmentin in the treatment of urinary tract infection and lower respiratory tract infection in a children's hospital", Proc Eur Symp on Augmentin, Scheveningen Jun. 1982, 1983: pp. 325–333.

Fraschini et al., "Pharmacokinetics and Tissue Distribution of Amoxicillin plus Clavulanic Acid after Oral Administration in Man", Journal of Chemotherapy, 1990, 2(3), 171–177.

Heikkinen et al., "Short–term use of amoxicillin–clavulanate during upper respiratory tract infection for prevention of acute otitis media", The Journal of Peds, Feb. 1995, 126(2), 313–316.

Hoberman et al., "Equivalent efficacy and reduced occurrence of diarrhea from a new formulation etc.", Journal of Pediatric Infect. Dis., 1997, 16, pp. 463–470.

Hoberman et al., "Efficacy of amoxicillin/clavulanate for acute otitis media: relation to *Streptococcus pneumoniae* susceptibility", Pediatr Infect Dis Jr., 1996(15), pp. 955–962.

Jacobsson et al., "Evaluation of Amoxicillin Clavulanate Twice Daily versus Thrice Daily in the Treatment of Otitis Media in Children", Eur. J. Clin. Microbiol. Infect. Dis., May 1993, pp. 319–324.

Jeffries et al., "An Initial Assessment of Augmentin for the Treatment of Paediatric Infections in General Practice", The British Journal of Clinical Practice, 1996, pp. 61–66.

Klein et al., "Antimicrobial Agents", Therapeutics—Part V, 1992, pp. 2179–2198.

Kucer et al., "Ampicillin–like penicillins—Amoxycillin, Epicillin, Cyclacillin, Hetacillin, Pivampicillin, Telampicillin, Bacampicillin and Metampicillin", 2) "Clavulanic Acid", The Use of Antibiotics, 1987, pp. 172–195/271–286.

Lachman et al., "Tablet Granulations", The Theory and Practica of Industrial Pharmacy, 1986, pp. 314–320.

Lerk et al., "Interaction of lubricants and colioidal silica during mixing with excipients", Pharmacuetica Acta Helvetiae, 1997, 52(3) pp. 33–39.

Lieberman et al., "Pharmaceutical Dosage Forms—Tablets Second Edition, Revised and Expanded", 1989, vol. 2, pp. 317–334.

McLaren et al., "A comparison of the efficacy and tolerability of Augmentin 625 mg po bd versus Augmentin 375 mg po tds in the tratment of acute bacterial exacerbations of chronic bronchitis", British Journal Clin Research, 1994 (5) pp. 1–10.

Neu, H. C., "Other B–Lactam Antibiotics", Principles and Practica of infectious Diseases, 1990, pp. 257–263.

Okhamapet et al., "Characterization of moisture interactions in some aqueous–based tablet film coating formulations", Journal Pharm Pharmacol, 1985(37), pp. 385–390.

Parrott, "Densification of Powders by Concavo–Convex Roller Compactor", Journal of Pharm Sciences, Mar. 1981, vol. 70(3), pp. 288–291.

Robinson, "Amoxicillin trihydrate/Clavulanate acid potassium salt", Med. Actual., 1982, 18(5) pp. 213–219.

Ruberto et al., "Amoxycillin and Clavulanic Acid in the Treatment of Urinary Tract Infections in Children", Journal of International Medical Research, 1989, 17, pp. 168–171.

Saarnivaara et al., "Effect of Storage on the Properties of Acetyisalicylc Acid Tablets Coated with Aqueous Hydroxypropyl Methyl–Cellulose Dispersion", Drug Develop and Ind Pharmacy, 1985, 11(2&3), pp. 481–492.

Sakellariou et al., "An evaluation of the interaction and plasticizing efficiency of the polyethylene glycols in ethyl cellulose and hydroxypropyl methylcellulose films using the torsional braid pendulum", Int Journal of Pharm, 1986(31), pp. 55–64.

Todd et al., "Amoxycillin/Clavulanic Acid—An Update of its Antibacterial Activity, Pharmcolinetic Properties and Therapeutic Use", Drugs, 1990, 39(2), pp. 264–307.

Toh, "Amoxycillin with clavulanic acid", The Austalian Nurses Journal, Dec./Jan. 1995, vol. 18, No. 6, Abstract.

Tondachi et al., "Tablet Coating in an Aqueous System", Drug Develop and Ind Pharmacy, 1977, 3(3), pp. 227–240.

van Niekerk, "Pharmacokinetic Study of a Paediatric Formulation of Amoxycillin and Clavulanic Acid in Children", European Journal of Clinical Pharmacology, 1985, 29, pp. 235–239.

Repertorio Fermaceutico Italiano, 3rd Edition 1989, A106 to A108. (Translation Included).

Vidal 1994, 70th Edition, pp. 132–134 (Translation included).

Prescribing for Children, British National Formulary, vol. 29, p. 11, (1995).

Beta–Lactamase Inhibitors, The Pharmacological Basis of Therapeutics, eighth edition, p. 1093., 1990.

Craig, et al., "Killing and Regrowth of Bacteria in Vitro: A Review", Scand J Infect Dis., 1991, Suppl 74, pp. 63–70.

Dagan, et al., "Bacteriologic and clinical efficacy of high dose amoxicillin/clavulanate in children with acute otitis media", Pediatric Infectious Diseases Journal, 2001,vol. 20, pp. 828–837.

Lister et al., "Rationale behind High–Dose Amoxicillin Theraphy for Acute Otitis Media Due to Penicillin–Nonsusceptible Pnsumococci: Support from In Vitro Pharmacodynamic Studies", Antimicrobial Agents and Chemotherapy, Sep. 1997, vol. 41, No. 9, pp. 1926–1932.

Woodnutt, G. and Parker D.S. (1978) Rabbit liver acetyl–CoA synthetase. Biochem J. 175, 757–759.

Woodnutt, G. and Parker D.S. (1979) Acetate entry rate into portal and peripheral blood in the rabbit. Proc. Nutr. Soc. 38, 724.

Everett J.R., Jennings K.R., Woodnutt G. and Buckingham M.J. (1984) Spin echo NMR spectroscopy: A new method for studying penicillin metabolism. Chem Commun, 894–895.

Everett J.R., Jennings K. and Woodnutt G. (1985) $^{19}$F–NMR spectroscopy study of the metabolites of flucloxacillin in rat urine. J. Pharm. Pharmacol. 37, 869–873.

Woodnutt G. and Parker D.S. (1986) Acetate metabolism by tissues of the rabbit. Comp. Biochem. Physiol. 85B, 487–490.

Woodnutt, G., Kernutt I. and Mizen L. (1987) Pharmacokinetics and distribution of ticarcillin–ciavualnic acid (Timentin) in experimental animals. Antimicrobial Agents and Chemotherapy 31, 1826–1830.

Woodnutt G., Catherall E.J., Kernutt I. and Mizen L. (1988) Temocillin efficacy in experimental Klebsiella pneumoniae meningitis after Infusion into rabbit plasma to simulate antibiotic concentrations in human serum. Antimicrobial Agents and Chemotherapy 32, 1705–1709.

Mizen L. and Woodnutt G. (1988) A critique of animal pharmacokinetics. Journal of Antimicrobial Chemotherapy 21, 273–280.

Woodnutt G., Kernutt I. and Mizen L. (1989) Penetration of Augmentin and Timentin into lymph after simulation of human serum pharmacokinetics in the rabbit. J. Drug Devel. 2, Suppl. 1, 123–126.

Catherall E., Woodnutt G. and Mizen L. (1989) Distribution and efficacy studies with ticarcillin–clavulanic aid (Timentin) in experimental *Klebsiella pneumoniae* meningitis in rabbits. J. Drug Devel. 2, Suppl. 1, 127–130.

Woodnutt G., Catherall E.J., Kernutt I. and Mizen L. (1989) Influence of simulated human pharmacokinetics on the efficacy of temocillin against a *Klebsiella pneumoniae* meningitis infection in the rabbit. J. Chemother. Suppl. 4, 475–476.

Mizen L. Woodnutt G., Kernutt I. and Catherall E. (1989) Simulation of human serum pharmacokinetics of ticarcillin–clavulanic acid and ceftazidime in rabbits, and efficacy against experimental *Klebsiella pneumoniae* meningitis. Antimicrobial Agents and Chemotherapy 33, 693–699.

Everett J. R., Tyler, J.W. and Woodnutt G. (1989) A study of flucloxacillin metabolites in rat urine by two–dimensional $^1$H, $^{19}$F Cosy NMR, Journal of Pharmaceutical and Biomedical Analysis, 7, 397–403.

Woodnutt G., Berry V., Kernutt I. and Mizen L. (1990) Penetration of amoxycillin, ticarcillin and clavulanic acid into lymph after intravenous infusion in rabbits to simulate human serum pharmacokinetics. Journal of Antimicrobial Chemotherapy 26, 695–704.

Slocombe B., Brown T.N., Cooper C.E., Catherall E. and Woodnutt G. (1990) in vitro and in vivo activity of temocillin. Research and Clinical Forums 12, 21–33.

Woodnutt G., Berry V. and Mizen L. (1992) Simulation of human serum pharmacokinetics of cefazolin, piperacillin, and BRL (42715 in rats and efficacy against experimental intraperitoneal infections. Antimicrobial Agents and Chemotherapy 36, 1427–1431.

Connor S.C., Everett J.R., Jennings, K.R., Nicholson J.K. and Woodnutt G. (1994) High resolution $^1$H NMR Spectroscopic studies of the metabolism and excretion of amplicillin in rats and amoxycillin in rats and man. J. Pharm. Pharmacol. 46, 128–134.

Woodnutt G., Berry V., Bryant J. Gisby J. and Siocombe B. (1995) Efficite de l'association amoxicilline–acide clavulanique dans un modele d'abces sous–cutane a *E. coli* chez le rat apres simulation de l'administration chez l'homme de 1g/200mg (perfusion). La lettre de l'infectiologie de la microbiologie a la clinique. Numero hors–serie. 23–26.

Burgess W.J., Bryant J. and Woodnutt G. (1995) Uptake of clavulanic acid across rat jejunal segments in vitro. J. Physiology, 482, 41P.

Berry V., Jennings K. and Woodnutt G. (1995) Bactericidal and morphological effects of amoxicillin on Helicobacter pylor. Antimicrobial Agents and Chemotherapy 39, 1859–1861.

Mizen, L., V. Berry and G. Woodnutt. (1995) The influence of uptake from the gastrointestinal tract and first pass effect on oral bioavailability of (Z)–alkyloxyimino penicillins. J. Pharm. Pharmacol. 47, 725–730.

Woodnutt G., Berry V.J. and Mizen L.W. (1995) The effect of protein binding on the penetration of beta–lactams into rabbit peripheral lymph. Antimicrobial Agents and Chemotherapy 39, 2678–2683.

Berry V., Thorburn C.E., Tyler J. and Woodnutt G. (1998) Bacteriological efficacy of three macrolides compared with amoxicillin/clavulanate against *S. pneumoniae* and *H. influenzae*. Antimicrobial Agents and Chemotherapy 42, 3193–3199.

Woodnutt G. and Berry V. (1999) The use of two pharmacodynamic models to assess the efficacy of amoxicillin/clavulanate against experimental respiratory tract infections caused by strains of *S. pneumoniae*. Antimicrobial Agents and Chemotherapy 43, 29–34.

Ji Y., Marra A., Rosenberg M and Woodnutt G. (1999) Regulated antisense RNA eliminates alpha–toxin virulence in *Stahylococcus aureus* Infection. J. Bact. 181, 6585–6590.

Hannan P. and Woodnutt G. (2000) in vitro activity of gemifloxacin (SB–265805; LB20304a) against human mycoplasmas. J. Antimicrob. Chemother. 45, 367–369.

Berry V., Page R., Satterfield J., Straub R. and Woodnutt G. (2000) Comparative in vivo activity of gemifloxacin in a rat model of respiratory infection. J. Antimicrob. Chemother. 45, *Suppl. S1*, 79–85.

Berry V., Page R., Satterfield J., Singley C., Straub R. and Woodnutt G. (2000) Comparative efficacy of gemifloxacin in experimental models of pyelonephritis and wound infection. J. Antimicrob. Chemother 45, *Suppl. S1*, 87–93.

Woodnutt G. (2000) Pharmacodynamics to Combat Resistance. J. Antimicrob. Chemother. 46, Suppl. T1, 25–31.

Brooks G., Burgess W., Colthurst D., Hinks J.D., Hunt E., Pearson M.J., Shea B., Takle A.K., Wilson J.M. and Woodnutt G. (2001) Pleuromutillins. Part 1: The identification of novel mutilin 14–carbamates. Bioorganic and Medicinal Chemistry 9, 1221–1231.

Ji Y., Zhang B., Van Horn S.F., Warren P., Woodnutt G., Burnham M.K.R. and Rosenberg M. (2001) Identification of critical staphlococcal genes using conditional phenotypes generated by antisense RNA. Science 293, 2266–2269.

Barry et al., "Effect of Increased Dosages of Amoxycillin in Treatment of Experimental Middel Ear Otitis Due to Penicillin–Resistant Streptococcus pneumoniae", Antibacterial Agents and Chemotherapy, Aug. 1993, vol. 37, No. 8, pp. 1599–1603.

Craig, "Antimicrobial Resistant Issues of the Future", Diagn Microbiol Infect Dis, 1996, 25, pp. 213–217.

Craig et al., "Pharmacokinetics and pharmacodynamics of antibiotics in otitis media", Pediatr Infect Dis J, 1996, pp. 255–259.

Finch, "Pneumonia: The Impact of Antibiotic Resistance on its Management", Microbial Drug Resistance, vol. 1, No. 2, 1995, pp. 149–158.

Friedland et al., "Management of Infections caused by Antibiotic–Resistant Streptococcus Pneumoniae", The New England Journal of Medicine, 1994, vol. 331, No. 6, pp. 377–382.

Jacobson et al., "Evaluation of Amoxicillin Clavulanate Twice Daily versus Thrice Daily in the Treatment of Otitis Media in Children", Eur. J. Clin. Microbiol. Infect. Dis., May 1993, pp. 319–324.

McCracken, "Emergence of resistant Streptococcus pneumoniae: a problem in pediatrics", Pediatr Infect Dis J, 1995, 14, pp. 424–428.

Pankuch et al., "Comparative activity of ampicillin, amoxycillin, amoxycillin/clavulanate and cefotaxime against 189 penicillin susceptible and –resistant pneumococci", Journal of Antimicrobial Chemotherapy, 1995, 35, 883–888.

Martindale, The Extra Pharmacopoeia, Thirtieth Edition, Edited by James E. F. Reynolds (London, The Pharmaceutical Press, 1993), pp. 115–116 and 148.

Merck Index 1989, 610 and 2342.

1996 MIMS Annual, Twentieth Edition, May 1995, pp. 8–476 to 8–477.

Textbook of Pediatric Infectious Diseases, 3rd Edition, vol. II, Editors R. D. Feigin and J. D. Cherry, pp. 2179–2198, (1995).

Calver et al., "Dosing of Amoxicillin/Clavulanate Given Every 12 Hours Is as Effective as Dosing Every 8 Hours for Treatment of Lower Respiratory Tract Infection", Clinical Infectious Disease, 1997, 24, pp. 570–574.

Calver et al., "Augmentin Bid Versus Augmentin TID in the Treatment of Lower Respiratory Tract Infections", Can. J. Infect. Dis, 1995, vol. 6, Suppl C, Abstract 0338, p. 239C.

Calver et al., "Amoxicillin/Clavulanate BID vs A/C TID in the Treatment of Lower Respiratory Tract Infections", Abstracts of the 35th ICAAC, 1995, p. 334.

Moonsammy et al., "Improved Safety Profile of a New Amoxicillin/Clavulanate Adult BID Formulation Compared with the Standard A/C TID Formulation", Abstracts of the 36th ICAAC, 1996, p. 290.

* cited by examiner

PHARMACEUTICAL FORMULATION

This application is a 371 of PCT/US96/14554 filed Sep. 5, 1996 which claims the benefit under 35 U.S.C. § 119(e) of provisional application No. 60/003,353, filed Sep. 7, 1995.

This invention relates to pharmaceutical formulations comprising amoxycillin and a salt of clavulanic acid (hereinafter termed "clavulanate" unless a specific salt is identified).

The combination of amoxycillin and clavulanate is an effective empirical treatment for bacterial infections and may be administered by oral dosing, for instance in the form of tablets, and, for paediatric formulations, aqueous solutions or suspensions, typically as a flavoured syrup.

Clavulante is a β-lactamase inhibitor and is included with the β-lactam antibiotic amoxycillin to counter a β-lactamase mediated resistance mechanism. Some microrganisms such as Streptococcus pneumoniae have resistance mechanisms which are not β-lactamase mediated. WO94/16696 discloses generally that potassium clavulanate may enhance the effectiveness of beta-lactam antibiotics such as amoxycillin against microorganisms having a resistance mechanism which is not β-lactamase mediated.

Streptococcus pneumoniae is an important pathogen in respiratory tract infection in the community. S pneumoniae is the most commonly implicated bacterium in the important respiratory tract infections of otitis media in paediatrics and sinusitis in patients of all ages and acute exacerbations of bronchitis and pneumococcal pneumonia in adults. There have been increasing reports in Europe and the U.S. of the emergence of DRSP (drug-resistant Streptococcus pneumoniae) with decreased suspectibility to β-lactam and other antibiotics.

Whilst confirmed cases of DRSP infection may be successfully treated with relatively high levels of amoxycillin, there still remains the need to develop effective empiric treatments, where DRSP may be suspected, for instance in an area with a high prevalence of DRSP, but where other, β-lactamase producing, organisms may also be present.

It has now been found that empiric treatment of infections potentially caused by DRSP may be successfully treated with formulations of co-amoxiclav which have a relatively large amount of amoxycillin.

Accordingly, the present invention provides a pharmaceutical formulation adapted for oral administration comprising amoxycillin and clavulanate in a weight ratio between 10:1 and 20:1 inclusive in combination with a pharmaceutically acceptable carrier or excipient.

Such formulations are of use for the empiric treatment of infections, potentially caused by DRSP, in particular respiratory tract infections such as otitis media in paediatrics and sinusitis in patients of all ages and acute exacerbations of bronchitis and pneumococcal pneumonia in adults.

The invention also provides for the use of amoxycillin and clavulanate in a ratio of between 10:1 and 20:1 inclusive in the manufacture of a medicament for oral administration for the empiric treatment of infections potentially caused by DRSP in human patients.

The invention also provides a method for the empiric treatment of infections potentially caused by DRSP in a human patient comprising the oral administration to a patient in need thereof of a pharmaceutical formulation comprising amoxycillin and clavulanate in a weight ratio between 10:1 and 20:1 inclusive.

The formulations of the present invention are suitable for use with patients of all ages, including adult, older children and and paediatric patients.

The weight ratios of amoxycillin:clavulanate expressed herein are as free acid equivalent. Preferred amoxycillin:clavulanate ratios are between 12:1 to 16:1 inclusive, especially about 14:1±5%.

In the formulations of the invention the amoxycillin is preferably in the form of amoxycillin trihydrate, although sodium amoxycillin, for example the crystalline form of sodium amoxycillin which is disclosed in EP 0131147 A may also be used.

Clavulanate is preferably in the form of potassium clavulanate. Potassium clavulanate is extremely moisture-sensitive and should be stored and handled in conditions of 30% RH or less, ideally as low as possible. Solid dosage forms should be packaged in atmospheric moisture-proof containers, and such forms and/or their containers may contain a desiccant.

The formulations of the invention may be made up into solid dosage forms for oral administration by a method conventional to the art of pharmaceutical technology, e.g. tablets or powder or granular products for reconstitution into a suspension or solution. Suitable ingredients and suitable methods for making such tablets are disclosed in for example GB 2 005 538-A, WO 92/19227 and WO 95/28927. Powder or granular formulations, such as paediatric suspension formulations, may be manufactured using techniques which are generally conventional in the field of manufacture of pharmaceutical formulations and in the manufacture of dry formulations for reconstitution into such suspensions. For example a suitable technique is that of mixing dry powdered or granulated ingredients for loading into a suitable container.

For paediatric dosing, the formulations of the invention are preferably made up into a sweet flavoured aqueous syrup formulation of generally conventional formulation (except for its novel amoxycillin : clavulanate ratio and intended use) containing a suitable weight of the amoxycillin and clavulanate in a unit dose volume, e.g. 5 ml or 2.5 ml of the syrup. Because of the water-sensitivity of clavulanate it is preferred to provide such a syrup formulation as dry powder or granules contained in an atmospheric moisture-proof container or sachet for make up with water or other suitable aqueous medium shortly prior to use.

The formulation of this invention will normally, in addition to its active materials amoxycillin trihydrate and potassium clavulanate, also include excipients which are standard in the field of formulations for oral dosing and used in generally standard proportions, and at generally standard particle sizes and grades etc.

In the case of paediatric oral suspensions, these excipients may comprise suspending aids, glidants (to aid filling), diluents, bulking agent, flavours, sweeteners, stabilisers, and in the case of dry formulations for make up to an aqueous suspension, an edible desiccant to assist preservation of the potassium clavulanate against hydrolysis by atmospheric moisture on storage. Potassium clavulanate is normally supplied in admixture with silicon dioxide as diluent.

Suitable excipients for use include xantham gum (suspension aid), colloidal silica (glidant), succinic acid (stabiliser), aspartame (sweetener), hydroxypropylmethylcellulose (suspension aid) and silicon dioxide (desiccant, diluent for potassium clavulanate and bulking agent). Flavours may comprise common flavours such as orange, banana, raspberry and golden syrup, or mixtures thereof, to suit local requirements.

Generally the proportion of active materials amoxycillin trihydrate and potassium clavulanate in a dry formulation for make up with aqueous media into a solution, suspension or syrup formulation of the invention may be around 30–80 wt %.

The present invention therefore also provides a process for manufacture of a formulation as described above.

The formulations of the invention may be adapted to paediatric dosing, i.e. to patients aged between 3 months to 12 years. Such formulations may be dosed in daily quantities up to the maximum normal permitted dose of amoxycillin and clavulanate.

A suitable dosage quantity of the formulation of the invention for paediatric patients is 75 to 115 mg/kg amoxycillin per day and 5 to 7.5 mg/kg of clavulanate per day. Suitably, the dosage is administered bid, for example in two, preferably equal, unit doses per day, suitably around 12 hours apart. A suitable dosage for use in such a regimen is 90±10%, especially ±5%, mg/kg amoxycillin and 6.4±10%, especially ±5%, mg/kg clavulanate (i.e. nominally a 14:1 ratio) per day.

Suitably, paediatric formulations as hereinbefore described are provided which comprise from 500 to 700, preferably about 600 mg of amoxycillin/5 ml of formulation when reconstituted and from 35 to 50 mg, preferably about 43 mg of clavulanic acid/5 ml of formulation when reconstituted.

For older children and adult patients these quantities may be increased pro rata. A suitable dosage for use in such a regimen is 3500±10%, especially ±5%, mg amoxycillin and 250±10%, especially ±5%, mg clavulanate (i.e. nominally a 14:1 ratio) per day, preferably administered bid, for example in two, preferably equal, unit doses per day, suitably around 12 hours apart.

The formulation of the invention may for example be provided in solid unit dose forms embodying suitable quantities for the administration of such a daily dose. For example a unit dosage form may be tablets, or sachets containing granules or powders for reconstitution, one or two of which are to be taken at each bid dosing interval. Alternatively a unit dose may be provided as a bulk of solid or solution or suspension, e.g. as a syrup for paediatric administration, together with a suitable measuring device of known type to facilitate administration of a suitable unit dose quantity of the formulation. A suitable unit dose quantity is one which enables the administration of the above-mentioned daily dosage quantity divided between two bid doses.

For paediatric patients, a suitable unit dose quantity is preferably one which enables the administration of the above-mentioned daily dosage quantity, divided between two bid doses, e.g. half of the above-mentioned daily dose, in a volume of a solution or suspension suitable for oral administration to a paediatric patient, preferably of between 2.5 to 10 ml, preferably as a syrup. A paediatric formulation may therefore comprise a bulk of a solution or suspension, e.g. a syrup, or granules or powder which can be made up into such a solution or suspension, at a concentration of solution or suspension which contains such a dose in such a volume.

The present invention therefore also provides the above described formulation provided for administration in such doses.

For adults, a suitable unit dose may be provided in a tablet. Suitably, for a bid dosage regimen based on 1750 mg amoxycillin/125 mg clavulanate per unit dose, this may conveniently be provided as two tablets, one comprising amoxycillin and clavulanate and a second comprising amoxycillin alone. Accordingly, in a further aspect, the present invention provides for a unit dosage of 1750 mg amoxycillin and 125 mg clavulante provided by two tablets, one comprising 875 mg amoxycillin and 125 mg clavulanate and a second comprising 875 mg amoxycillin. A suitable tablet comprising 875 mg amoxycillin and 125 mg clavulanate is marketed by SmithKline Beecham in several countries and is also described in WO 95/28927 (SmithKline Beeecham).

The invention will now be described by way of example only with reference to FIGS. 1, 2 and 3 which show graphically the results of Example 3 below.

EXAMPLE 1

Paediatric Formulation

Figure 1:
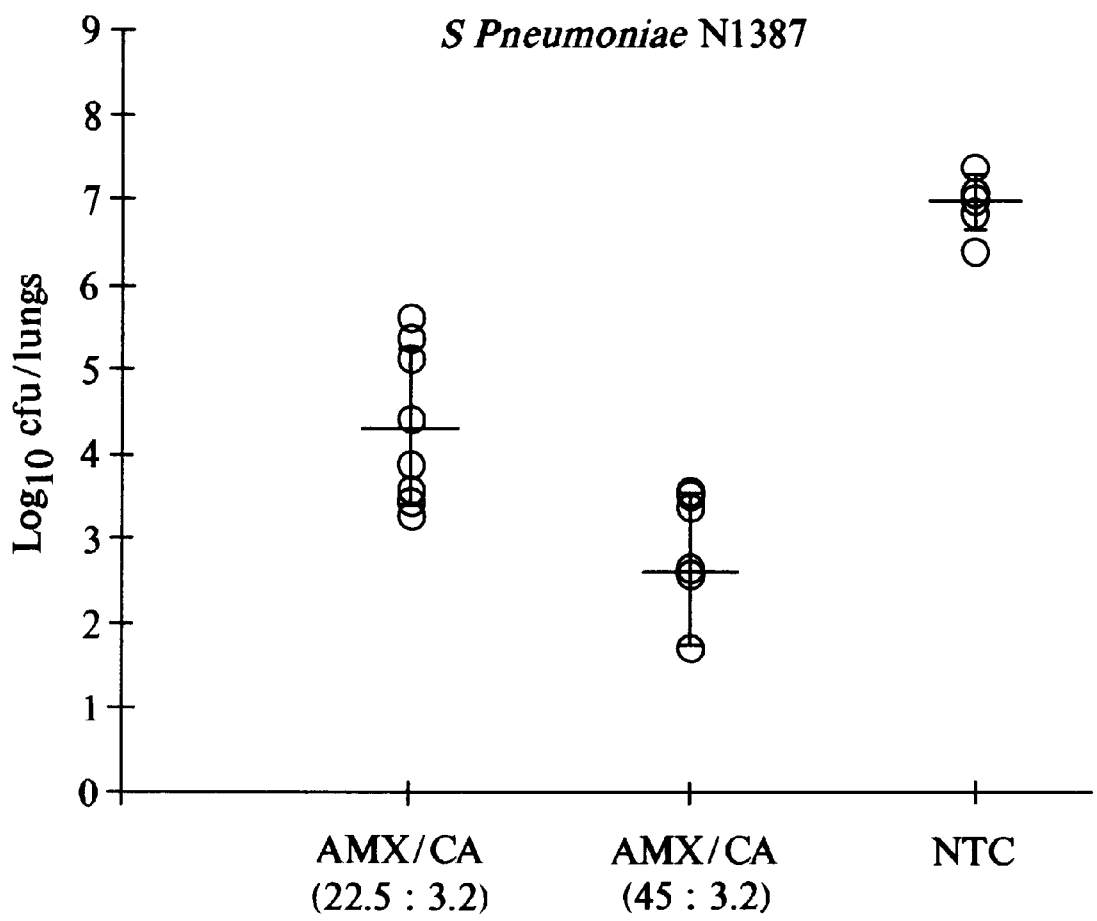
FIGS. 1, 2 and 3 show respectively $Log_{10}$ of colony forming units ("cfu") of S Pneumoniae strains N1387, 14319 and 410101 per lungs observed in rats following dosing with an amoxycillin: potassium clavulanate ("AMX:CA") formulation of this invention administered at 45:3.2 mg/kg amoxycillin:clavulanic acid equivalent, a comparison formulation administered at 22.5 3.2 mg/kg, and a non-treated control ("NTC") as described below.

The following paediatric formulation comprising 600 mg amoxicillin and 42.9 mg clavulanic acid in 5 ml of suspension when reconstituted:

| Ingredient | Quantity (mg) |
| --- | --- |
| Amoxycillin trihydrate | 697.00* |
| (equivalent to amoxicillin free acid) | 600.00 |
| Potassium Clavulanate/Syloid 1:1 blend | 113.00** |
| (equivalent to clavulanic acid, including 8% overage) | 46.332 |
| Xanthan Gum | 12.500 |
| Aspartame | 12.500 |
| Succinic acid | 0.835 |
| Colloidal silicon dioxide | 25.00 |
| Hydroxypropyl methyl cellulose | 79.650 |
| Flavours | 72.500 |
| Silicon dioxide | 86.315*** |
| Total fill weight | 1100.00 |

*based on 86% potency as amoxicillin free acid
**based on 41% potency as clavulanic acid in potassium clavulante/Syloid 1:1 blend, including an 8% overage
***quantity of silicon dioxide (Syloid) varies, according to quantities of amoxycillin trihydrate and potassium clavulanate/Syloid blend, such that total fill weight remains constant at 1100.00 mg Bottles are filled with 23.92 g of formulated powder and then reconstituted with 84 ml of water immediately prior to use, to give 100 ml of suspension.

EXAMPLE 2

Tablet Formulation

A tablet formulation comprising 875 mg amoxycillin and 125 mg clavulanate was prepared having the following composition:

| Ingredient | (mg.) | wt. % |
| --- | --- | --- |
| Active Constituents | | |
| Amoxycillin trihydrate | 1017.4 | 70.2 |
| (equivalent to amoxycillin) | 875.00 | |
| Potassium clavulanate | 152.45 | 10.5 |

-continued

| Ingredient | (mg.) | wt. % |
|---|---|---|
| (equivalent to clavulanic acid) | 125.0 | |
| Other Constituents | | |
| Magnesium Stearate | 14.50 | 1.00 |
| Sodium Starch Glycollate | 29.00 | 2.00 |
| Colloidal Silicon Dioxide | 10.0 | 0.70 |
| Microcrystalline Cellulose | 226.65 | 15.6 |
| Core tablet weight | 1450.00 | 100.00 |

The tablets are made by blending the amoxycillin, potassium clavulanate, and portions of microcrystalline cellulose and magnesium stearate, roller compacting this blend, then blending with the other constituents, before tabletting on a conventional tablet press and coating. The tablet core is coated with a film (Opadry White YS-1-7700/Opadry White OY-S-7300 ex Colorcon) from an aqueous solvent system, to give tablets with a nominal coated weight of 1482 mg. Further details of how the tablets are manufactured are provided in WO 95/28927 (SmithKline Beecham).

Similar tablets can be made in which the roller compaction step is replaced by slugging and /or a final film coating is applied from an organic solvent system such as dichloromethane rather than an aqueous solvent system.

A tablet formulation comprising 875 mg amoxycillin was prepared having the following composition:

| Core components | (mg/tablet) |
|---|---|
| Amoxicillin trihydrate | 1017.4 (875 fa) |
| Crospovidone, NF | 30.5 |
| Microcrystalline cellulose, NF | 204.4 |
| Sodium starch glycollate, NF | 26.0 |
| Colloidal Silicon Dioxide, NF | 8.7 |
| Magnaesium stearate, NF | 13.0 |
| Film Coat | |
| Opadry Pink | 39.0 |

The tablets are made by blending the amoxycillin and portions of microcrystalline cellulose and magnesium stearate, roller compacting this blend, then blending with the other constituents, before tabletting on a conventional tablet press and coating.

EXAMPLE 3

Biological Data—In Vivo Rat Model

Methodology.

Animals were anaesthetised and the external jugular vein was cannulated for administration of compounds. At least 48 h later animals were infected by intra-bronchial instillation of a 50 microliter inoculum of S Pneumoniae by non surgical intubation. Inocula were prepared in cooled molten nutrient agar with a final inoculum of approximately $10^6$ cfu in 50 microliters of agar. Dosing commenced 24 h after infection and compounds were administered as a continuous infusion into the jugular vein designed to simulate in rat plasma the concentration versus time curves obtained in human serum following oral administration of amoxycillin/clavulanate. For each organism tested, three groups of animals were used. The first two groups received amoxycillin and clavulanate to simulate bid dosing of this combination at either 22.5/3.2 mg/kg (a 7:1 ratio) or 45/3.2 mg/kg (a 14:1 ratio) to children.

The remaining group received an infusion of saline at a rate similar to the dosed groups and acted as infected non-treated controls. Dosing continued for 2–5 days, and 14 days after therapy ended the animals were killed and lungs removed aseptically for bacteriological assessment.

Results

Table 1 shows the MIC's of amoxycillin, amoxycillin:clavulanate and penicillin G for the three resistant strains of S Pneumoniae tested.

TABLE 1

| | MIC (mcg/ml) | | |
|---|---|---|---|
| Strain | Amoxycillin | Amox:clav. | Penicillin G |
| N1387 | 2 | 2 | 2 (R) |
| 14319 | 4 | 4 | 8 (R) |
| 410101 | 4 | 4 | 4 (R) |

*Streptococcus Pneumoniae* N1387:

Bacterial numbers in the lungs of saline-treated animals were $6.97\pm0.30$ $\log_{10}$ cfu/lungs. Both doses of amoxycillin:clavulanate reduced the numbers of viable bacteria in the lungs significantly compared with control animals ($4.37\pm0.93$ $\log_{10}$ cfu/lungs and $2.62+0.85$ $\log_{10}$ cfu/lungs for the 7:1 and 14:1 ratios respectively; p<0.01). However as shown in FIG. 1 amoxycillin:clavulanate at the 14:1 bid ratio was significantly more effective than when administered at the lower ratio of 7:1.

Figure 2:
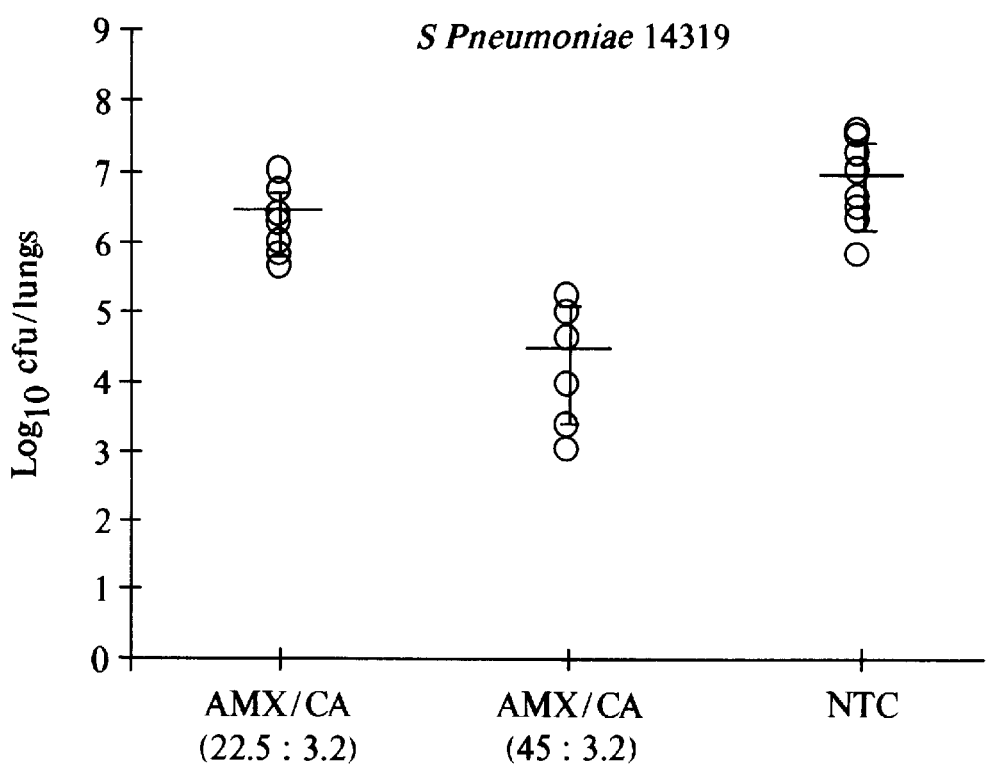

*Streptococcus Pneumoniae* 14319:

Bacterial numbers in the lungs of saline-treated animals were $6.8\pm0.62$ $\log_{10}$ cfu/lungs. Amoxycillin: clavulanate at the 7:1 ratio reduced the numbers of viable bacteria in the lungs ($6.26\pm0.47$ $\log_{10}$ cfu/lungs) but this reduction did not reach significance compared with control animals. However as shown in FIG. 2 amoxycillin:clavulanate at the 14:1 ratio bid reduced the bacterial count to $4.28\pm0.82$ $\log_{10}$ cfu/lungs such that this dose was significantly more effective than control animals and animals treated with the lower ratio of 7:1.

*Streptococcus Pneumonlae* 410101.

Figure 3:
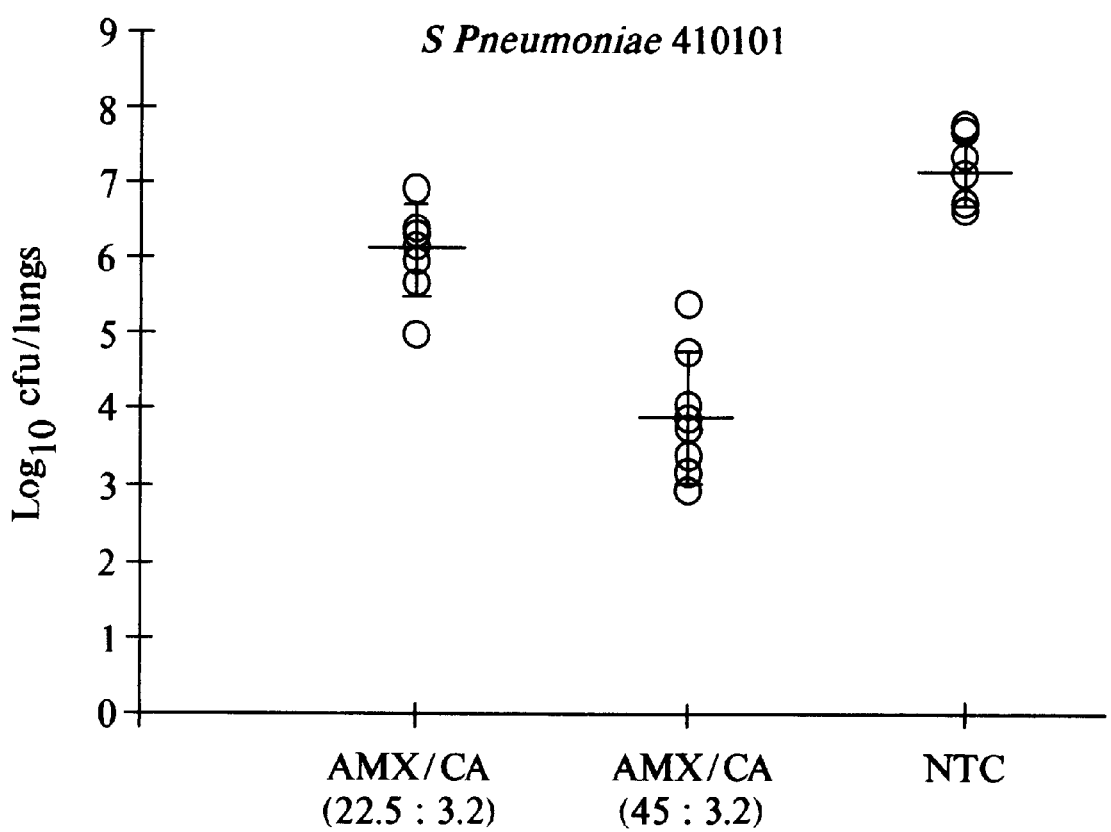

Bacterial numbers in the lungs of saline-treated animals were $7.11\pm0.45$ $\log_{10}$ cfu/lungs. Amoxycillin:clavulanate at the 7:1 ratio reduced the numbers of viable bacteria in the lungs ($6.14\pm0.6$ $\log_{10}$ cfu/lungs) significantly compared with control animals (p,0.05). However as shown in FIG. 3 amoxycillin: clavulanate at the 14:1 ratio bid reduced the counts to $3.91\pm0.81$ $\log_{10}$ cfu/lungs and was significantly more effective than animals treated with the lower ratio of 7:1.

What is claimed is:

1. A method for the empiric treatment of infections potentially caused by DRSP in a human patient in need thereof, comprising the oral administration to said patient of a pharmaceutical formulation comprising amoxycillin and clavulanate in which the dosage amount is from $90\pm10\%$ mg/kg of amoxycillin per day and $6.4\pm10\%$ mg/kg of clavulanate per day, said dosage amount being administered in divided doses twice daily.

2. The method according to claim 1 in which the dosage amount is $90\pm5\%$ mg/kg of amoxycillin per day and $6.4\pm5\%$ mg/kg of clavulanate per day.

3. The method according to claim 2 in which the dosage amount is about 90 mg/kg of amoxycillin per day and about 6.4 mg/kg of clavulanate per day.

4. The method according to any one of claims 1, 2, or 3 wherein the amoxycillin is amoxycillin trihydrate and the clavulanate is potassium clavulanate.

5. The method according to claim 4 wherein the patient is a pediatric patient.

6. The method according to claim 1 wherein the formulation is a tablet, or a powder or granular product for reconstitution.

7. The method according to claim 1 wherein the formulation is a liquid aqueous syrup or suspension.

8. A method of treating otitis media in a patient in need thereof which comprises administering to said patient a pharmaceutical formulation comprising a dosage amount of 90±10% mg/kg of amoxycillin per day and 6.4±10% mg/kg of clavulanate per day, said dosage amount being administered in divided doses twice daily.

9. The method according to claim 8 in which the dosage amount is 90±5% mg/kg of amoxycillin per day and 6.4±5% mg/kg of clavulanate per day.

10. The method according to claim 9 in which the dosage amount is about 90 mg/kg of amoxycillin per day and about 6.4 mg/kg of clavulanate per day.

11. The method according to any one of claims 8, 9, or 10 wherein the amoxycillin is amoxycillin trihydrate and the clavulanate is potassium clavulanate.

12. The method according to claim 11 wherein the patient is a pediatric patient.

13. The method according to claim 8 wherein the formulation is a tablet, or a powder or granular product for reconstitution.

14. The method according to claim 8 wherein the formulation is a liquid aqueous syrup or suspension.

15. A method of treating sinusitis in a patient in need thereof which comprises administering to said patient a pharmaceutical formulation comprising a dosage amount of 90±10% mg/kg of amoxycillin per day and from 6.4±10% mg/kg of clavulanate per day, said dosage amount being administered in divided doses twice daily.

16. The method according to claim 15 in which the dosage amount is 90±5% mg/kg of amoxycillin per day and 6.4±5% mg/kg of clavulanate per day.

17. The method according to claim 16 in which the dosage amount is about 90 mg/kg of amoxycillin per day and about 6.4 mg/kg of clavulanate per day.

18. The method according to any one of claims 15, 16, or 17 wherein the amoxycillin is amoxycillin trihydrate and the clavulanate is potassium clavulanate.

19. The method according to claim 18 wherein the patient is a pediatric patient.

20. The method according to claim 15 wherein the formulation is a tablet, or a powder or granular product for reconstitution.

21. The method according to claim 15 wherein the formulation is a liquid aqueous syrup or suspension.

22. A method of treating a respiratory infection in a patient in need thereof, which comprises administering to said patient a pharmaceutical formulation comprising a dosage amount of 90±10% mg/kg of amoxycillin per day and 6.4±10% mg/kg of clavulanate per day, said dosage amount being administered in divided doses twice daily.

23. The method according to claim 22 in which the dosage amount is 90±5% mg/kg of amoxycillin per day and 6.4±5% mg/kg of clavulanate per day.

24. The method according to claim 23 in which the dosage amount is about 90 mg/kg of amoxycillin per day and about 6.4 mg/kg of clavulanate per day.

25. The method according to any one of claims 22 to 24 wherein the amoxycillin is amoxycillin trihydrate and the clavulanate is potassium clavulanate.

26. The method according to claim 22 wherein the patient is a pediatric patient.

27. The method according to claim 22 wherein the formulation is a tablet, or a powder or granular product for reconstitution.

28. The method according to claim 22 wherein the formulation is a liquid aqueous syrup or suspension.

29. A method of treating infections caused by DRSP in a patient in need thereof, which comprises administering to said patient a pharmaceutical formulation comprising a dosage amount of 90±10% mg/kg of amoxycillin per day and 6.4±10% mg/kg of clavulanate per day, said dosage amount being administered in divided doses twice daily.

30. The method according to claim 29 in which the dosage amount is 90±5% mg/kg of amoxycillin per day and 6.4±5% mg/kg of clavulanate per day.

31. The method according to claim 30 in which the dosage amount is about 90 mg/kg of amoxycillin per day and about 6.4 mg/kg of clavulanate per day.

32. The method according to any one of claims 29 to 31 wherein the amoxycillin is amoxycillin trihydrate and the clavulanate is potassium clavulanate.

33. The method according to claim 32 wherein the patient is a pediatric patient.

34. The method according to claim 29 wherein the formulation is a tablet, or a powder or granular product for reconstitution.

35. The method according to claim 29 wherein the formulation is a liquid aqueous syrup or suspension.

36. A method of treating a *Streptococcus pneumoniae* infection in a patient in need thereof wherein the *Streptococcus pneumoniae* have a minimum inhibitory concentration value of 2 µg/ml, which comprises administering to said patient a pharmaceutical formulation comprising a dosage amount of 90±10% mg/kg of amoxycillin per day and 6.4±10% mg/kg of clavulanate per day, said dosage amount being administered in divided doses twice daily.

37. The method according to claim 36 in which the dosage amount is 90±5% mg/kg of amoxycillin per day and 6.4±5% mg/kg of clavulanate per day.

38. The method according to claim 37 in which the dosage amount is about 90 mg/kg of amoxycillin per day and about 6.4 mg/kg of clavulanate per day.

39. The method according to any one of claims 36 to 38 wherein the amoxycillin is amoxycillin trihydrate and the clavulanate is potassium clavulanate.

40. The method according to claim 39 wherein the patient is a pediatric patient.

41. The method according to claim 39 wherein the formulation is a tablet, or a powder or granular product for reconstitution.

42. The method according to claim 39 wherein the formulation is a liquid aqueous syrup or suspension.

43. A method of treating a *Streptococcus pneumoniae* infection in a patient in need thereof wherein the *Streptococcus pneumoniae* have a minimum inhibitory concentration value of 4 µg/ml, which comprises administering to said patient a pharmaceutical formulation comprising a dosage amount of 90±10% mg/kg of amoxycillin per day and 6.4±10% mg/kg of clavulanate per day, said dosage amount being administered in divided doses twice daily.

44. The method according to claim 43 in which the dosage amount is 90±5% mg/kg of amoxycillin per day and 6.4±5% mg/kg of clavulanate per day.

45. The method according to claim 44 in which the dosage amount is about 90 mg/kg of amoxycillin per day and about 6.4 mg/kg of clavulanate per day.

46. The method according to any one of claims 43 to 45 wherein the amoxycillin is amoxycillin trihydrate and the clavulanate is potassium clavulanate.

47. The method according to claim 46 wherein the patient is a pediatric patient.

48. The method according to claim 43 wherein the formulation is a tablet, or a powder or granular product for reconstitution.

49. The method according to claim 43 wherein the formulation is a liquid aqueous syrup or suspension.

50. A method for the empiric treatment of infections caused by bacterial infections in a human patient in need thereof, comprising the oral administration to said patient of a pharmaceutical formulation comprising amoxycillin and clavulanate in which the dosage amount is 90±10% mg/kg of amoxycillin per day and 6.4±10% mg/kg of clavulanate per day, said dosage amount being administered in divided doses twice daily.

51. The method according to claim 50 in which the dosage amount is 90±5% mg/kg of amoxycillin per day and 6.4±5% mg/kg of clavulanate per day.

52. The method according to claim 51 in which the dosage amount is about 90 mg/kg of amoxycillin per day and about 6.4 mg/kg of clavulanate per day.

53. The method according to any one of claims 50 to 52 wherein the amoxycillin is amoxycillin trihydrate and the clavulanate is potassium clavulanate.

54. The method according to claim 53 wherein the patient is a pediatric patient.

55. The method according to claim 50 wherein the formulation is a tablet, or a powder or granular product for reconstitution.

56. The method according to claim 50 wherein the formulation is a liquid aqueous syrup or suspension.

\* \* \* \* \*